US008519116B2

(12) United States Patent
Wirtz et al.

(10) Patent No.: US 8,519,116 B2
(45) Date of Patent: Aug. 27, 2013

(54) METHOD FOR PREDICTING A CLINICAL RESPONSE OF A PATIENT SUFFERING FROM OR AT RISK OF DEVELOPING CANCER TOWARDS A GIVEN MODE OF TREATMENT

(75) Inventors: Ralph Markus Wirtz, Köln (DE); Wolfgang Michael Bruckl, Spardorf (DE)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 0 days.

(21) Appl. No.: 12/989,969

(22) PCT Filed: Mar. 27, 2009

(86) PCT No.: PCT/EP2009/053680
§ 371 (c)(1),
(2), (4) Date: Oct. 28, 2010

(87) PCT Pub. No.: WO2009/132909
PCT Pub. Date: Nov. 5, 2009

(65) Prior Publication Data
US 2011/0039275 A1 Feb. 17, 2011

(30) Foreign Application Priority Data

Apr. 29, 2008 (EP) .................................... 08008190

(51) Int. Cl.
*C07H 21/04* (2006.01)
*C07H 21/02* (2006.01)
*C12Q 1/68* (2006.01)

(52) U.S. Cl.
USPC ................... 536/24.3; 536/24.31; 536/24.33; 536/23.1; 435/6.12

(58) Field of Classification Search
None
See application file for complete search history.

(56) References Cited

U.S. PATENT DOCUMENTS

2004/0072227 A1* 4/2004 Jonak et al. ...................... 435/6
2006/0234237 A1 10/2006 Amler et al.

FOREIGN PATENT DOCUMENTS

WO 20060015742 2/2006
WO 20070112330 10/2007

OTHER PUBLICATIONS

The Gene Card for SPON2 found at http://www.genecards.org/cgi-bin/carddisp.pl?gene=SPON2&search=mindin accessed online Dec. 7, 2011.*
Thisted What is a P value? The University of Chicago 1998 http://www.stat.uchicago.edu/~thisted.*
Evans, William et al. Moving towards individualized medicine with pharmacogenomics. Nature 2004. vol. 429, pp. 464-468.*
Chan, Eric. Integrating Transcriptomics and Proteomics. G&P magazine 2006 vol. 6 No. 3 pp. 20-26.*
Hoshikawa, Yasushit et al. Hypoxia induces different genes in the lungs of rats compared with mice. Physical Genomics 2003 vol. 12 pp. 209-219.*
Whitehead, Andrew et al. Variation in tissue specific gene expression among natural populations. Genome Biology 2005 vol. 6 Issue 2 Article R13.*
Feinstein et al. Development 1999 vol. 196 pp. 3637-3648.*
Arya et al. Expert Rev. Mol. Diagn. 2005 vol. 5 No. 2 pp. 1-11.*
GenBank Accession NM_006108 GI: 110347422 (Feb. 11, 2008).*
GenBank Accession NM_012445 GI: 6912681 (Feb. 11, 2008).*
Parry Renate et al.: "Identification of a novel prostate tumor target, mindin/RG-1, for antibody-based radiotherapy of prostate cancer." Cancer Research vol. 54, No. 18, Sep. 15, 2005, pp. 8397-8405.
Kitagawa, M et al.: "Effect of F-Spondin on cementoblastic differentiation of human periodontal ligament cells." Biochemical and Biophysical Research Communications, Academic Press Inc. Orlando, FL, US. vol. 349, No. 3, Oct. 27, 2006, pp. 1050-1056.
Feinstein Yael et al: "The Neuronal Class 2 TSR Proteins F-Spondin and Mindin: A Small Family With Divergent Biological Activities." The International Journal of Biochemistry and Cell Biology, vol. 36, No. 6, Jun. 2004, pp. 975-980.
Oikonomopoulou, K. et al.:"Prediction of ovarian cancer prognosis and response to chemotherapy by a serum-based multiparametric biomarker panel." British Journal of Cancer, vol. 99, No. 7, Oct. 7, 2008, pp. 1103-1113.
International Search Report for PCT/EP09/053680 dated Oct. 7, 2009.

* cited by examiner

*Primary Examiner* — Amanda Haney

(57) ABSTRACT

The present invention relates to a method for predicting a clinical response of a patient suffering from or at risk of developing cancer, preferably colorectal cancer, towards a given mode of treatment, the method including the steps of: a) obtaining a biological sample from the patient; b) determining the expression level of at least SPON-2, and optionally determining the expression level of SPON-1, in the sample; c) comparing the expression level or expression levels determined in (b) with one or several reference expression levels; and d) predicting therapeutic success for the given mode of treatment in the patient or implementing therapeutic regimen in the patient from the outcome of the comparison in step (c).

1 Claim, 3 Drawing Sheets

Figure 1:
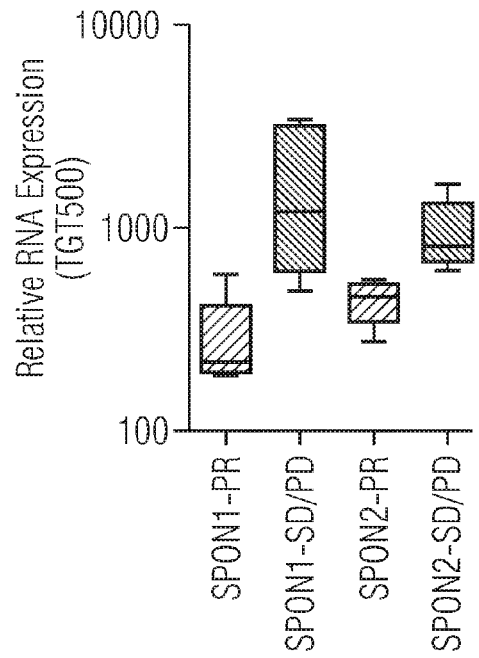

METHOD FOR PREDICTING A CLINICAL RESPONSE OF A PATIENT SUFFERING FROM OR AT RISK OF DEVELOPING CANCER TOWARDS A GIVEN MODE OF TREATMENT

FIELD OF THE INVENTION

The present invention relates to methods for prediction of the therapeutic success of cancer, preferably colorectal cancer, therapy.

BACKGROUND OF THE INVENTION

Colorectal cancer (CRC) represents the second leading cause of cancer related deaths in the European Union (Eucan, Cancer Mondial Database 1998). One million people worldwide are diagnosed with this cancer annually, about half of them will succumb, mostly to metastatic disease (Globocan, Cancer Mondial Database 1998). Though much is known about the genetic pathways leading to colorectal neoplasia, the exact molecular mechanisms underlying tumor growth, local invasion, angiogenesis, intravasation and finally metastasis remain poorly understood. Moreover, the relevance of these mechanisms for therapy success or failure have not been resolved and prognostic/predictive markers helping to guide therapy decisions have not yet been identified or validated for clinical routine usage with sufficient level of evidence. Although much effort has been made to develop an optimal clinical treatment course for an individual patient with cancer, only little progress could be achieved predicting the individual's response to a certain therapy.

About 75% percent of patients who are diagnosed with CRC undergo curative treatment. The long term survival of CRC patients depends on the local tumor stage and the potential development of synchronous or metachronous distant metastases. The 5-year-survival rate of CRC patients exceeds 90% in the UICC stage I (limited invasion without regional lymph node metastasis), but decreases to below 20% in the UICC stage IV (presence of distant metastasis). Neoadjuvant and adjuvant chemotherapeutic and radiotherapeutic strategies are used to prevent locoregional and distant recurrences, but are effective only in a fraction of stage IV CRC patients. Chemotherapy can lead to a partial remission of distant metastases and can enable secondary palliative surgeries and thereby result in long-term survival. Approximately 25,000 metastatic colorectal cancer patients receive palliative chemotherapy in Germany every year. Clinical decisions on the therapeutic procedure and extent of resectional treatment in colorectal carcinoma are presently based on imaging and on conventional histopathological features. The diagnostic accuracy of these approaches is limited, which leads to surgical interventions that are most often more radical than required, or to chemotherapeutic treatment of patients who do not benefit from this harsh regimen.

Using high-dose 5-FU and folinic acid (FA) as a 24-h infusion (AIO schedule) in patients with non-resectable metastases it could been shown, that after downsizing, secondary curative metastatic resection was technically feasible in 11% of those patients (Wein et al., 2001)[1]. Owing to the introduction of irinotecan (a semisynthetic camptothecin, which inhibits topoisomerase I), and oxaliplatin (a third generation platinum compound) which are administered in combination with infusional 5-FU/FA as first-line treatment for metastatic colorectal carcinoma (mCRC), the number of responders varied between 45% and 56% and median survival durations of between 19.5 and 21.5 months could be achieved (Goldberg et al., 2006)[2]. Therefore, infusional therapy with 5-FU/FA alone or in combination with either oxaliplatin or irinotecan is actually recommended by the therapy guidelines of the German Cancer Society (Deutsche Krebsgesellschaft) as standard therapy for mCRC. Recently, bevacizumab, a monoclonal antibody directed against vascular endothelial growth factor (VEGF), showed efficacy in addition to irinotecan and (bolus) 5-FU/FA and is approved for first-line treatment of mCRC (Hurwirz, 2004)[3]. However, as more drugs are added, as more toxicity will be induced. Furthermore, there is an economic aspect which has to be considered. While an eight weeks first line chemotherapy in mCRC consisting of 5-FU and FA as an infusional regimen (e.g DeGramont schedule) costs 263$ per patient, an eight weeks therapy with first 5-FU, FA, oxaliplatin and bevacizumab is worth 21,033$ per patient (Schrag, 2004)[4].

F-spondin (SPON-1, Spondin 1) has been identified as a protein expressed and secreted at high levels in the floor plate, a cell group implicated in the control of neural cell pattern and axonal growth in the developing vertebrate nervous system. The bovine homolog of F-spondin has been identified independently as VSGP (Vascular smooth muscle cell growth-promoting factor). M-spondin (SPON-2, Spondin 2, DIL-1, DIL1, Mindin) is an extracellular matrix protein highly homologous to F-spondin.

It has been shown from several studies that the epidermal growth factor receptor (EGFR) plays an important role in cancer genesis. Said receptor, also named ErbB-1, is a cell-surface receptor for members of the epidermal growth factor family (EGF-family) of extracellular protein ligands. The epidermal growth factor receptor is a member of the ErbB family of receptors, a subfamily of four closely related receptor tyrosine kinases: EGFR (ErbB-1), HER2/c-neu (ErbB-2), Her 3 (ErbB-3) and Her 4 (ErbB-4). It has been reported that mutations affecting EGFR expression or activity often result in cancer.

EGFR is a transmembrane protein receptor which is activated by binding of its specific ligands, including epidermal growth factor and transforming growth factor $\alpha$ (TGF$\alpha$). Upon activation by its growth factor ligands, EGFR undergoes a transition from an inactive monomeric form to an active homodimer, which then stimulates cell growth, tissue proliferation and cell mitosis, the mechanism of which will be described in the following.

The said EGFR comprises a tyrsoine kinase on its intracellular domain. EGFR dimerization stimulates the activity of said tyrosine kinase. As a result, autophosphorylation of five tyrosine (Y) residues in the C-terminal domain of EGFR occurs. These are Y992, Y1045, Y1068, Y1148 and Y1173. This autophosphorylation elicits downstream activation and signaling by several other proteins that associate with the phosphorylated tyrosines through their own phosphotyrosine-binding SH2 domains. These downstream signaling proteins initiate several signal transduction cascades, principally the MAPK, Akt and JNK pathways, leading to DNA synthesis and cell proliferation (Shepherd, 2005)[5].

Such proteins modulate phenotypes such as cell migration, adhesion, and proliferation. The kinase domain of EGFR can also cross-phosphorylate tyrosine residues of other receptors it is aggregated with, and can itself be activated in that manner. One of the major effects of EGFR autophosphorylation is the upregulation of the expression of the Vascular Endothelial Growth Factor (VEGF), which, when being secreted, stimulates, among others, cell proliferation, particularly angiogenesis.

There is some evidence that in some cases preformed inactive dimers may also exist before ligand binding. In addition to forming homodimers after ligand binding, EGFR may pair with another member of the ErbB receptor family, such as ErbB2/Her-2/neu, to create an activated heterodimer. Moreover, there is evidence that in some cancerogenic cells the overexpression of EGFR leads to an elevated abundance of said receptor in the cellular membranes, which leads to autonomous dimerization due to high receptor density, without the need for the ligand to elicit said dimerization.

Hence, an overexpression of either native or mutant EGFR due is frequently found in cancerogenic and pre-cancerogenic cells and/or tissues. Said overexpression may be accompanied by mutations of the EGFR gene itself, as well as to gene amplification, polysomy, aneuploidy, genomic instability and the like. Said overexpression leads to a self-activation of cell proliferation in the respective cells and/or tissues due to autonomous dimerization, as well as to the enhanced secretion of VEGF, which in turn stimulates cell proliferation in the very same cells and/or tissues, as well as to an enhanced vascularization of the respective tissue due to an enhanced angiogenesis. Overexpression of EGFR does thus trigger a positive feedback mechanism which rapidly enforces tumor growth.

It is yet difficult to determine those tumor types which are promoted by EGFR overexpression. This is due to the fact that an overexpression rate of 2×, which is often enough to promote the above identified phenomena leading to increased malignancy of the tumor, can not be resolved with standard methods, i.e immunohistochemistry (IHC), fluorescent in situ hybridization (FISH) and/or quantitative PCR.

This means that, in tumor diagnosis, many tumor types which are characterized by enhanced EGFR expression and/or EGFR overexpression and are thus potential targets for EGFR inhibitors might remain undetected with standard methods. Hence, chances to treat these tumors with the most adequate treatments available to date are lost.

As EGFR is a member of the ErbB receptor family, it can be assumed that the above mentioned mechanism are also applicable to the other ErbB receptors introduced above.

Similiarly, overexpression VEGFA is frequently found in cancerogenic and pro-cancerogenic lesions, primary tumors and/or metatstatic lesions thereof. Said overexpression may be accompanied by enhanced receptor tyrosin kinase activities of tumor and/or adjacent stroma cells. VEGFA and it's family members may act as an autocrine or paracrine stimulus leading to enhanced cell proliferation, cell migration, repair capacity and or cell survival. Depending on the presence of receptors for said ligands VEGF factors may act on tumor cells, endothelial cells or other components of the stroma. Drugs inhibiting the VEGF ligand and VEGF receptor induced activities have been developed, such as small molecule inhibitors (e.g. Sutent® and Nexaxar®) or antibodies (e.g. Avastin®). However, similar to the situation described above for EGFR family members, their expression is difficult to reliably assess by standard technologies like immunohostochemistry and mRNA analysis methods like DNA microarrays or PCR methodologies. In part this is due to the limited dynamic range of the expression levels leading to different tumorbiological behaviour. However, it is part of this invention to indirectly measure these tumors having VEGF activities by measuring SPON-1 and SPON-2.

As VEGFA is a member of the VEGF (Vascular endothelial growth factor) and related to the PDGF (Platelet derived growth factor) and FGF (Fibrobast growth factor) family, it can be assumed that the above mentioned mechanisms are also applicable to the other growth factors of said families.

As VEGFR1 is a member of the VEGFR (Vascular endothelial growth factor receptor) family, it can be assumed that the above mentioned mechanisms are also applicable to the other growth factors of said families, including the PDGFR and FGF Receptor family.

Response to chemotherapy is comparatively low with about 10%-30% patients having benefit from treatment, while having serious side effects and being costly for the national health systems. However, molecular tests that better select a more appropriate therapy, for instance by adding targeted anti-cancer drugs, are not available yet.

Therefore, there is a strong need for predictive factors for defining responsiveness to chemotherapy and for selecting a more appropriate therapy, respectively, such as a medication related to the signalling pathway of receptors from the ERB receptor family.

Definitions

The term "prediction", as used herein, relates to an individual assessment of the malignancy of a tumor, or to the expected survival rate (DFS, disease free survival) of a patient, if the tumor is treated with a given therapy. In contrast thereto, the term "prognosis" relates to an individual assessment of the malignancy of a tumor, or to the expected survival rate (DFS, disease free survival) of a patient, if the tumor remains untreated.

The term "clinical response" of a patient, as used herein, relates to the effectiveness of a certain therapy in a patient, meaning an improvement in any measure of patient status, including those measures ordinarily used in the art, such as overall survival, progression free survival, recurrence-free survival, and distant recurrence-free survival.

The term "neoplastic disease" refers to a cancerous tissue this includes carcinomas, (e.g., carcinoma in situ, invasive carcinoma, metastatic carcinoma) and pre-malignant conditions, neomorphic changes independent of their histological origin (e.g. ductal, lobular, medullary, mixed origin).

The terms "cancer" and "cancerous" refer to or describe the physiological condition in mammals that is typically characterized by unregulated cell growth. The term "cancer" as used herein includes carcinomas, (e.g., carcinoma in situ, invasive carcinoma, metastatic carcinoma) and pre-malignant conditions, neomorphic changes independent of their histological origin. The term "cancer" is not limited to any stage, grade, histomorphological feature, invasiveness, aggressiveness or malignancy of an affected tissue or cell aggregation. In particular stage 0 cancer, stage I cancer, stage II cancer, stage III cancer, stage IV cancer, grade I cancer, grade II cancer, grade III cancer, malignant cancer and primary carcinomas are included. Examples of cancers include, but are not limited to colorectal cancer, lung cancer, ovarian cancer, cervical cancer, stomach cancer, pancreatic cancer, head and neck cancer and/or breast cancer.

The term "tumor" as used herein, refers to all neoplastic cell growth and proliferation, whether malignant or benign, and all pre-cancerous and cancerous cells and tissues.

The term "determining the status" as used herein, refers to a measurable property of a gene and its products, especially on the nucleotide level and the gene level including mutation status and gene expression status. A number of parameters to determine the status of a gene and its products can be used including, but not limited to, determining the level of protein expression, the amplification or expression status on RNA level or DNA level, of polynucleotides and of polypeptides, and the analysis of haplotype or the mutation status of the gene. An exemplary determinable property correlated with the status of estrogen receptor or progesterone receptor is the amount of the estrogen receptor or progesterone receptor RNA, DNA or other polypeptide in the sample or the presence of nucleotide polymorphisms.

The terms "biological sample", as used herein, refer to a sample obtained from a patient. The sample may be of any biological tissue or fluid. Such samples include, but are not limited to, sputum, blood, serum, plasma, blood cells (e.g., white cells), tissue, core or fine needle biopsy samples, cell-containing body fluids, free floating nucleic acids, urine, peritoneal fluid, and pleural fluid, or cells there from. Biological samples may also include sections of tissues such as frozen or fixed sections taken for histological purposes or microdissected cells or extracellular parts thereof. A biological sample to be analyzed is tissue material from neoplastic lesion taken by aspiration or punctuation, excision or by any other surgical method leading to biopsy or resected cellular material. Such biological sample may comprise cells obtained from a patient. The cells may be found in a cell "smear" collected, for example, by a nipple aspiration, ductal lavage, fine needle biopsy or from provoked or spontaneous nipple discharge. In another embodiment, the sample is a body fluid. Such fluids include, for example, blood fluids, serum, plasma, lymph, ascitic fluids, gynecological fluids, or urine but not limited to these fluids.

The term "therapy modality", "regimen" or as well as "therapeutic regimen" refers to a timely sequential or simultaneous administration of anti-tumor, and/or immune stimulating, and/or blood cell proliferative agents, and/or radiation therapy, and/or hyperthermia, and/or hypothermia for cancer therapy. The administration of these can be performed in an adjuvant and/or neoadjuvant mode. The composition of such "protocol" may vary in the dose of the single agent, timeframe of application and frequency of administration within a defined therapy window. Currently various combinations of various drugs and/or physical methods, and various schedules are under investigation.

By "array" or "matrix" is meant an arrangement of addressable locations or "addresses" on a device. The locations can be arranged in two dimensional arrays, three dimensional arrays, or other matrix formats. The number of locations can range from several to at least hundreds of thousands. Most importantly, each location represents a totally independent reaction site. Arrays include but are not limited to nucleic acid arrays, protein arrays and antibody arrays. A "nucleic acid array" refers to an array containing nucleic acid probes, such as oligonucleotides, polynucleotides or larger portions of genes. The nucleic acid on the array is preferably single stranded. Arrays wherein the probes are oligonucleotides are referred to as "oligonucleotide arrays" or "oligonucleotide chips." A "microarray," herein also refers to a "biochip" or "biological chip", an array of regions having a density of discrete regions of at least about 100/cm$^2$, and preferably at least about 1000/cm$^2$. The regions in a microarray have typical dimensions, e.g., diameters, in the range of between about 10-250 µm, and are separated from other regions in the array by about the same distance. A "protein array" refers to an array containing polypeptide probes or protein probes which can be in native form or denatured. An "antibody array" refers to an array containing antibodies which include but are not limited to monoclonal antibodies (e.g. from a mouse), chimeric antibodies, humanized antibodies or phage antibodies and single chain antibodies as well as fragments from antibodies.

The term "small molecule", as used herein, is meant to refer to a compound which has a molecular weight of less than about 5 kD and most preferably less than about 4 kD. Small molecules can be nucleic acids, peptides, polypeptides, peptidomimetics, carbohydrates, lipids or other organic (carbon-containing) or inorganic molecules. Many pharmaceutical companies have extensive libraries of chemical and/or biological mixtures, often fungal, bacterial, or algal extracts, which can be screened with any of the assays of the invention to identify compounds that modulate a bioactivity.

The terms "regulated" or "regulation" and "differentially regulated" as used herein refer to both upregulation [i.e., activation or stimulation (e.g., by agonizing or potentiating] and down regulation [i.e., inhibition or suppression (e.g., by antagonizing, decreasing or inhibiting)].

The term "transcriptome" relates to the set of all messenger RNA (mRNA) molecules, or "transcripts", produced in one or a population of cells. The term can be applied to the total set of transcripts in a given organism, or to the specific subset of transcripts present in a particular cell type. Unlike the genome, which is roughly fixed for a given cell line (excluding mutations), the transcriptome can vary with external environmental conditions. Because it includes all mRNA transcripts in the cell, the transcriptome reflects the genes that are being actively expressed at any given time, with the exception of mRNA degradation phenomena such as transcriptional attenuation. The discipline of transcriptomics examines the expression level of mRNAs in a given cell population, often using high-throughput techniques based on DNA microarray technology.

The term "expression levels" refers, e.g., to a determined level of gene expression. The term "pattern of expression levels" refers to a determined level of gene expression compared either to a reference gene (e.g. housekeeper or inversely regulated genes) or to a computed average expression value (e.g. in DNA-chip analyses). A pattern is not limited to the comparison of two genes but is more related to multiple comparisons of genes to reference genes or samples. A certain "pattern of expression levels" may also result and be determined by comparison and measurement of several genes disclosed hereafter and display the relative abundance of these transcripts to each other.

Alternatively, a differentially expressed gene disclosed herein may be used in methods for identifying reagents and compounds and uses of these reagents and compounds for the treatment of cancer as well as methods of treatment. The differential regulation of the gene is not limited to a specific cancer cell type or clone, but rather displays the interplay of cancer cells, muscle cells, stromal cells, connective tissue cells, other epithelial cells, endothelial cells of blood vessels as well as cells of the immune system (e.g. lymphocytes, macrophages, killer cells).

A "reference pattern of expression levels", within the meaning of the invention shall be understood as being any pattern of expression levels that can be used for the comparison to another pattern of expression levels. In a preferred embodiment of the invention, a reference pattern of expression levels is, e.g., an average pattern of expression levels observed in a group of healthy or diseased individuals, serving as a reference group.

"Primer pairs" and "probes", within the meaning of the invention, shall have the ordinary meaning of this term which is well known to the person skilled in the art of molecular biology. In a preferred embodiment of the invention "primer pairs" and "probes", shall be understood as being polynucleotide molecules having a sequence identical, complementary, homologous, or homologous to the complement of regions of a target polynucleotide which is to be detected or quantified. In yet another embodiment nucleotide analogues are also comprised for usage as primers and/or probes.

"Arrayed probes", within the meaning of the invention, shall be understood as being a collection of immobilized probes, preferably in an orderly arrangement. In a preferred embodiment of the invention, the individual "arrayed probes" can be identified by their respective position on the solid support, e.g., on a "chip".

The phrase "therapeutic success" refers, in the adjuvant chemotherapeutic setting to the observation of a defined tumor free or recurrence free survival time (e.g. 2 years, 4 years, 5 years, 10 years). This time period of disease free survival may vary among the different tumor entities but is sufficiently longer than the average time period in which most of the recurrences appear. In a neo-adjuvant therapy modality, response may be monitored by measurement of tumor shrinkage due to apoptosis and necrosis of the tumor mass.

The term "recurrence" includes distant metastasis that can appear even many years after the initial diagnosis and therapy of a tumor, or local events such as infiltration of tumor cells into regional lymph nodes, or occurrence of tumor cells at the same site and organ of origin within an appropriate time.

"Prediction of therapeutic success" does refer to the methods described in this invention. Wherein a tumor specimen is analyzed for it's gene expression and furthermore classified based on correlation of the expression pattern to known ones from reference samples. This classification may either result in the statement that such given tumor will develop recurrence and therefore is considered as a "non responding" tumor to the given therapy, or may result in a classification as a tumor with a prolonged disease free post therapy time.

The term "marker" refers to a biological molecule, e.g., a nucleic acid, peptide, protein, hormone, etc., whose presence or concentration can be detected and correlated with a known condition, such as a disease state.

The term "ligand", as used herein, relates to a molecule that is able to bind to and form a complex with a biomolecule to serve a biological purpose. In a narrower sense, it is an effector molecule binding to a site on a target protein, by intermolecular forces such as ionic bonds, hydrogen bonds and Van der Waals forces. The docking (association) is usually reversible (dissociation). Actual irreversible covalent binding between a ligand and its target molecule is rare in biological systems. Ligand binding to receptors often alters the chemical conformation, i.e. the three dimensional shape of the receptor protein. The conformational state of a receptor protein determines the functional state of a receptor. The tendency or strength of binding is called affinity. Ligands include substrates, inhibitors, activators, and neurotransmitters.

The term "agonist", as used herein, relates to a substance that binds to a specific receptor and triggers a response in the cell. It mimics the action of an endogenous ligand that binds to the same receptor.

The term "receptor", as used herein, relates to a protein on the cell membrane or within the cytoplasm or cell nucleus that binds to a specific molecule (a ligand), such as a neurotransmitter, hormone, or other substance, and initiates the cellular response to the ligand. Ligand-induced changes in the behavior of receptor proteins result in physiological changes that constitute the biological actions of the ligands.

The term "signalling pathway" is related to any intra- or intercellular process by which cells converts one kind of signal or stimulus into another, most often involving ordered sequences of biochemical reactions out- and inside the cell, that are carried out by enzymes and linked through hormones and growth factors (intercellular), as well as second messengers (intracellular), the latter resulting in what is thought of as a "second messenger pathway". In many signalling pathways, the number of proteins and other molecules participating in these events increases as the process emanates from the initial stimulus, resulting in a "signal cascade" and often results in a relatively small stimulus eliciting a large response.

The term "marker gene," as used herein, refers to a differentially expressed gene whose expression pattern may be utilized as part of a predictive, prognostic or diagnostic process in malignant neoplasia or cancer evaluation, or which, alternatively, may be used in methods for identifying compounds useful for the treatment or prevention of malignant neoplasia and colorectal cancer, lung cancer, ovarian cancer, cervical cancer, stomach cancer, pancreatic cancer, head and neck cancer and/or breast cancer in particular. A marker gene may also have the characteristics of a target gene.

"Target gene", as used herein, refers to a differentially expressed gene involved in cancer, preferably colorectal cancer, in a manner in which modulation of the level of the target gene expression or of the target gene product activity may act to ameliorate symptoms of cancer, preferably colorectal cancer. A target gene may also have the characteristics of a marker gene.

The term "expression level", as used herein, relates to the process by which a gene's DNA sequence is converted into functional protein and particularly to the amount of said conversion.

When used in reference to a single-stranded nucleic acid sequence, the term "substantially homologous" refers to any probe that can hybridize (i.e., it is the complement of) the single-stranded nucleic acid sequence under conditions of low stringency as described above.

The term "hybridization based method", as used herein, refers to methods imparting a process of combining complementary, single-stranded nucleic acids or nucleotide analogues into a single double stranded molecule. Nucleotides or nucleotide analogues will bind to their complement under normal conditions, so two perfectly complementary strands will bind to each other readily. In bioanalytics, very often labeled, single stranded probes are in order to find complementary target sequences. If such sequences exist in the sample, the probes will hybridize to said sequences which can then be detected due to the label. Other hybridization based methods comprise microarray and/or biochip methods. Therein, probes are immobilized on a solid phase, which is then exposed to a sample. If complementary nucleic acids exist in the sample, these will hybridize to the probes and can thus be detected. These approaches are also known as "array based methods". Yet another hybridization based method is PCR, which is described below. When it comes to the determination of expression levels, hybridization based methods may for example be used to determine the amount of mRNA for a given gene.

The term "a PCR based method" as used herein refers to methods comprising a polymerase chain reaction (PCR). This is an approach for exponentially amplifying nucleic acids, like DNA or RNA, via enzymatic replication, without using a living organism. As PCR is an in vitro technique, it can be performed without restrictions on the form of DNA, and it can be extensively modified to perform a wide array of genetic manipulations. When it comes to the determination of expression levels, a PCR based method may for example be used to detect the presence of a given mRNA by (1) reverse transcription of the complete mRNA pool (the so called transcriptome) into cDNA with help of a reverse transcriptase enzyme, and (2) detecting the presence of a given cDNA with help of respective primers. This approach is commonly known as reverse transcriptase PCR (rtPCR).

The term "determining the protein level", as used herein, refers to methods which allow the quantitative and/or qualitative determination of one or more proteins in a sample. These methods include, among others, protein purification, including ultracentrifugation, precipitation and chromatography, as well as protein analysis and determination, including the use protein microarrays, two-hybrid screening, blotting methods including western blot, mass spectrometry, one- and two dimensional gelelectrophoresis, isoelectric focusing and the like.

The term "anamnesis" relates to patient data gained by a physician or other healthcare professional by asking specific questions, either of the patient or of other people who know the person and can give suitable information (in this case, it is sometimes called heteroanamnesis), with the aim of obtaining information useful in formulating a diagnosis and providing medical care to the patient. This kind of information is called the symptoms, in contrast with clinical signs, which are ascertained by direct examination.

The term "etiopathology" relates to the course of a disease, that is its duration, its clinical symptoms, and its outcome.

OBJECT OF THE INVENTION

It is one object of the present invention to provide an improved method for the prediction of a clinical response of a patient suffering from or at a risk of cancer, preferably colorectal cancer, towards an agent to current status tests.

It is yet another object of the present invention to provide a method for the determination whether or not a tumor is likely to be susceptible to chemotherapy and a more appropriate therapy, respectively, in particular to a medication related to the signalling pathway of receptors from the ERB receptor family. In a preferred embodiment this refers to therapies targeting ERB receptor family members itself. In yet another embodiment this refers to gene products regulated by ERB family members and downstream activities thereof, such as family members of the VEGF/VEGFR and/or FGF/FGFR system.

These objects are met with methods and means according to the independent claims of the present invention. The dependent claims are related to preferred embodiments. It is yet to be understood that value ranges delimited by numerical values are to be understood to include the said delimiting values.

SUMMARY OF THE INVENTION

Before the invention is described in detail, it is to be understood that this invention is not limited to the particular component parts of the devices described or process steps of the methods described as such devices and methods may vary. It is also to be understood that the terminology used herein is for purposes of describing particular embodiments only, and is not intended to be limiting. It must be noted that, as used in the specification and the appended claims, the singular forms "a," "an" and "the" include singular and/or plural referents unless the context clearly dictates otherwise. It is moreover to be understood that, in case parameter ranges are given which are delimited by numeric values, the ranges are deemed to include these limitation values.

According to the invention, a method is provided for predicting a clinical response of a patient suffering from or at risk of developing cancer, preferably colorectal cancer, towards a given mode of treatment, said method comprising the steps of:
a) obtaining a biological sample from said patient;
b) determining the expression level of at least SPON-2, and optionally determining the expression level of SPON-1, in said sample;
c) comparing the expression level or expression levels determined in (b) with one or several reference expression levels; and
d) predicting therapeutic success for said given mode of treatment in said patient or implementing therapeutic regimen in said subject from the outcome of the comparison in step (c).

In a preferred embodiment of the present invention, said cancer is selected from the group comprising colorectal cancer, lung cancer, ovarian cancer, cervical cancer, stomach cancer, pancreatic cancer, head and neck cancer and/or breast cancer.

In an especially preferred embodiment of the present invention, said cancer is colorectal cancer. Preferably, said colorectal cancer is a stage III or stage IV colorectal cancer, in particular a primary tumor.

In another preferred embodiment of the present invention, it is provided that upregulated expression of SPON-1 and/or SPON-2 is indicative of a poor prediction as regards therapeutic success for patients receiving a chemotherapy.

In another preferred embodiment of the present invention, it is provided that
a) upregulated expression of SPON-1 and/or SPON-2 is indicative of a poor prediction as regards therapeutic success for stage IV colorectal cancer patients receiving a chemotherapy; and/or
b) upregulated expression of SPON-1 and/or SPON-2 is indicative of a recurrence for stage III colorectal tumors in cancer patients receiving a chemotherapy.

It is known that overexpression of SPON-1 indicates poor response to chemotherapy and worse overall survival in stage IV colorectal cancer (Brueckl et al., 2007)[6].

The inventors of the present invention found that there is a trend in a yet small stage III tumor cohort indicating SPON-1 to predict early recurrence despite adjuvant chemotherapy treatment.

Moreover, a combination analysis of SPON-1 and SPON-2 provides an improved method to predict response to chemotherapy on expression profiling.

In particular, they have found that high expression of SPON-2 not only significantly discriminates non-responding from responding stage IV colorectal tumors but also recurrent versus non-recurrent stage III colorectal tumors. Particularly, the results regarding stage III tumors are superior to the results obtained by using SPON-1.

In another preferred embodiment of the present invention, it is provided that upregulated expression of SPON-1 and/or SPON-2 is indicative of a promising prediction as regards therapeutic success for patients receiving a therapeutic regimen targeting the signalling pathway of receptors from the VEGF receptor and/or ligand family.

It is assumed that both endothelial cell and smooth muscle cell growth factors are highly expressed in areas undergoing significant angiogenesis. Since angiogenesis is also required to support tumor growth, the inventors of the present invention suggest to determine the expression level of at least SPON-2, optionally combined with the expression level of SPON-1, in a sample to predict response to therapeutic regimen targeting the signalling pathway of receptors from the VEGF receptor and/or ligand family.

In another preferred embodiment of the present invention, it is provided that upregulated expression of SPON-1 and/or SPON-2 is indicative of a promising prediction as regards therapeutic success for patients receiving a therapeutic regimen targeting the signalling pathway of receptors from the ErbB receptor and/or ligand family.

In another preferred embodiment of the present invention, it is provided that the mode of treatment for which prediction is sought is a treatment related to the signalling pathway of receptors from the ErbB receptor and/or ligand family.

The ErbB family of receptors, comprises four closely related receptor tyrosine kinases, namely
- EGFR (ErbB-1) (epidermal growth factor receptor), also known as ErbB-1 or HER1
- HER2 (ErbB-2; Her-2/neu),
- HER3 (ErbB-3), and
- HER4 (ErbB-4).

There is evidence that any of these receptors may be related to cancer genesis, as well as to an enhanced expression of VEGF factors. However, a preferred receptor of the method according to the invention is EGFR, as there is
- a number of medicaments available which relate to the EGFR signalling pathway,
- the interaction between EGFR and VEGF expression has been clearly demonstrated,
- the role of EGFR in tumor genesis is well known, and
- the therapeutic effect of tumor medication directed to the EGFR signalling pathway has been demonstrated.

The PDGF family of growth factors comprises several members which all have in common that they feature a cystine-knot domain, and bind to tyrosine kinase receptors, like those from the ErbB family. The VEGF family comprises members of the VEGF sub-family, i.e.
- VEGF-A,
- VEGF-B,
- VEGF-C,
- VEGF-D.

and the Placenta growth factor (PlGF), as well as Platelet derived growth factors (PDGF-A and PDGF-B).

A number of other VEGF-related proteins have also been discovered encoded by viruses (VEGF-E) and in the venom of some snakes (VEGF-F).

All of these growth factors are ligands which are related to the ErbB signalling pathway, as their expression level is upregulated upon activation or self activation of a receptor of the ErbB family, particularly of EGFR. The growths factors do thus meet the above identified definition according to which the said ligand is related to the signalling pathway of receptors from the ErbB receptor family.

In another preferred embodiment of the present invention, it is provided that the mode of treatment for which prediction is sought is a treatment related to the signalling pathway of receptors from the VEGF receptor and/or ligand family.

In yet another preferred embodiment of the present invention, it is provided that said given mode of treatment (a) acts on recruitment of lymphatic vessels, cell proliferation, cell survival, cell repair mechanisms and/or cell motility, and/or b) comprises administration of a chemotherapeutic agent.

Furthermore, it is provided in another preferred embodiment of the present invention that said given mode of treatment comprises chemotherapy, in particular palliative chemotherapy, administration of small molecule inhibitors, antibody based regimen, anti-proliferation regimen, pro-apoptotic regimen, pro-differentiation regimen, radiation and/or surgical therapy.

In another embodiment of the present invention, method of selecting a therapy modality for a patient afflicted with cancer, preferably colorectal cancer, is provided, said method comprising the steps of:
a) obtaining a biological sample from said patient;
b) predicting from said sample, by the method according to any one of the above methods, therapeutic success for a plurality of individual modes of treatment; and
c) selecting a mode of treatment which is predicted to be successful in step (b).

In another preferred embodiment of the present invention, it is provided that determining the expression level comprises:
a) determining the RNA expression level; and/or
b) determining the protein expression level.

It is particularly preferred that, in the method according to the invention, the said expression level is determined by
a) a hybridization based method;
b) a PCR based method;
c) determining the protein level, and/or by
d) an array based method.

In yet another preferred embodiment of the present invention, it is provided that the expression level of at least one of the said marker genes is determined with rtPCR (reverse transcriptase polymerase chain reaction) of the related mRNA.

In this preferred embodiment, the mRNA related to the markers is determined, namely with a reverse transcriptase polymerase chain reaction approach.

The inventors of the present invention have surprisingly found out that the determination of the marker genes' mRNA levels is very informative for the prediction of the clinical response of a patient suffering from or at risk of developing cancer, preferably colorectal cancer, towards a medicament.

In this context, it seems much more promising to provide anti-ErbB/anti-EGFR treatments, if so indicated, than anti-PDGF/anti-VEGF treatments (for example the anti-VEGF antibody Bevacizumab), because, in the signalling pathway, ErbB/EGFR is located upstream of PDGF/VEGF. This means that, if ErbB/EGFR is inhibited, a number of processes located downstream in the signalling pathway may be suppressed, among which VEGF-induced processes are only one example.

VEGF-related processes may be considered as one symptom out of a range of several symptoms related to tumor genesis, whereas defects in EGFR expression may be considered as the underlying cause for these symptoms, the treatment of which seems thus to be much more promising than the treatment of just one of said symptoms.

In addition, it can be concluded that combined anti-ErbB/anti-EGFR treatments and anti-PDGF/anti-VEGF treatments may be most promising in this situation.

In another preferred embodiment of the present invention, it is provided that the expression level of at least one of the said marker genes is determined in formalin and/or paraffin fixed tissue samples.

In yet another preferred embodiment of the present invention, it is provided that the expression level of at least one of the said ligands or receptors is determined in serum, plasma or whole blood samples.

Routinely, in tumor diagnosis tissue samples are taken as biopsies form a patient and undergo diagnostic procedures. For this purpose, the samples are fixed in formalin and/or paraffin and are then examined with immunohistochemistry methods. The formalin treatment leads to the inactivation of enzymes, as for example the ubiquitous RNA-digesting enzymes (RNAses). For this reason, the mRNA status of the tissue (the so called transcriptome), remains undigested.

However, the formalin treatment leads to partial depolymerization of the individual mRNA molecules. For this reason, the current doctrine is that formalin fixed tissue samples can not be used for the analysis of the transcriptome of said tissue.

For this reason, it is provided in a preferred embodiment of the present invention that after lysis, the samples are treated with silica-coated magnetic particles and a chaotropic salt, in order to purify the nucleic acids contained in said sample for further determination.

Collaborators of the inventors of the present invention have developed an approach which however allows successful purification of mRNA out of tissue samples fixed in such manner, and which is disclosed, among others, in WO03058649, WO2006136314A1 and DE10201084A1, the content of which is incorporated herein by reference.

Said method comprises the use of magnetic particles coated with silica ($SiO_2$). The silica layer is closed and tight and is characterized by having an extremely small thickness on the scale of a few nanometers. These particles are produced by an improved method that leads to a product having a closed silica layer and thus entail a highly improved purity. The said method prevents an uncontrolled formation of aggregates and clusters of silicates on the magnetite surface whereby positively influencing the additional cited properties and biological applications. The said magnetic particles exhibit an optimized magnetization and suspension behavior as well as a very advantageous run-off behavior from plastic surfaces. These highly pure magnetic particles coated with silicon dioxide are used for isolating nucleic acids, including DNA and RNA, from cell and tissue samples, the separating out from a sample matrix ensuing by means of magnetic fields. These particles are particularly well-suited for the automatic purification of nucleic acids, mostly from biological body samples for the purpose of detecting them with different amplification methods.

The selective binding of these nucleic acids to the surface of said particles is due to the affinity of negatively charged nucleic acids to silica containing media in the presence of chaotropic salts like guanidinisothiocyanate. Said binding properties are known as the so called "boom principle". They are described in the European patent EP819696.

The said approach is particularly useful for the purification of mRNA out of formalin and/or paraffin fixed tissue samples. In contrast to most other approaches, which leave very small fragments behind that are not suitable for later determination by PCR and/or hybridization technologies, the said approach creates mRNA fragments which are large enough to allow specific primer hybridization and/or specific probe hybridization. A minimal size of at least 100 bp, more preferably 200 base pairs is needed for specific and robust detection of target gene expression. Moreover it is also necessary to not have too many inter-sample variations with regard to the size of the RNA fragments to guarantee comparability of gene expression results. Other issues of perturbance of expression data by sample preparation problems relate to the contamination level with DNA, which is lower compared to other bead based technologies. This of particular importance, as the inventors have observed, that DNAse treatment is not efficient in approximately 10% of FFPE samples generated by standard procedures and stored at room temperature for some years before cutting and RNA extraction.

The said approach thus allows a highly specific determination of candidate gene expression levels with one of the above introduced methods, particularly with hybridization based methods, PCR based methods and/or array based methods, even in formalin and/or paraffin fixed tissue samples, and is thus extremely beneficial in the context of the present invention, as it allows the use of tissue samples fixed with formalin and/or paraffin, which are available in tissue banks and connected to clinical databases of sufficient follow-up to allow retrospective analysis.

In another preferred embodiment of the present invention, it is provided that said treatment related to the signalling pathway of receptors from the ErbB receptor family comprises the administration of an agonist of the ErbB receptor domain.

In yet another preferred embodiment said treatment related to the signalling pathway of receptors from the ErbB receptor family comprises the administration of nucleotides, ribozomes, aptamers and/or nucleotide analogues capable of affecting the expression of ErbB receptor, VEGF receptor and/or VEGFA ligand expression. Preferably these substances act via downregulation of mRNA levels of said candidate genes.

However, also induction or elevation of gene expression by introduction of receptor gene expression (e.g. ERBB-4 and/or VEGFD expression) can be advantageous to counteract the tumorpromoting activity (e.g. of EGFR, Her-2/neu and/or VEGFC).

By way of illustration and not by way of restriction said agonists may be selected from the group consisting of Cetuximab (tradename Erbitux®, target receptor is EGFR), Matuzumab (EMD7200, target receptor is EGFR), Trastuzumab (tradename Herceptin®, target receptor is HER2/neu), Pertuzumab (target receptor is HER2/neu), Bevacizumab (tradename Avastin®, target ligand is VEGFA), 2C3 (target ligand is VEGFA), VEGF-trap (AVE-0005, target ligands are VEGFA and PIGF), IMC-1121B (target receptor is VEGFR2), and CDP-791 (target receptor is VEGFR2).

In yet another preferred embodiment said treatment related to the signalling pathway of receptors from the ErbB receptor family comprises the administration of a tyrosin kinase inhibitor.

In another preferred embodiment of the present invention, it is provided that said treatment related to the signalling pathway of receptors from the VEGF receptor family comprises the administration of an agonist of the VEGF receptor domain.

By way of illustration and not by way of restriction said inhibitors may be selected from the group consisting of Gefitinib (tradename Iressa®, ZD-1839, target receptor is EGFR), Erlotinib (tradename Tarceva®, OSI-774, target receptor is EGFR), EKB-569 (target receptor is EGFR), PKI-166 (target receptor is EGFR),), PKI-166 (target receptor is EGFR), Lapatinib (tradename tycerb®, target receptor is EGFR and Her-2/neu), GW572016 (target receptors are EGFR and Her-2/neu), AEE-788 (target receptors are EGFR, Her-2/neu and VEGFR-2), CI-1033 (target receptors are EGFR, Her-2/neu and Her4), and AZD6474 (target receptors are EGFR and VEGFR-2).

However, other treatments related to the ErbB receptor family signalling pathway which fall under the scope of the present invention comprise the administration of Sorafenib (tradename Nexavar®, BAY 43-9005, target receptors are VEGFR-2, VEGFR-3, c-KIT, PDGFR-B, RET and Raf-Kinase), BAY 57-9352 (target receptor is VEGFR-2), Sunitinib (tradename Sutent®, target receptors are VEGFR-1, VEGFR-2 and PDGFR), AG13925 (target receptors are VEGFR-1 and VEGFR-2), AG013736 (target receptors are VEGFR-1 and VEGFR-2), AZD2171 (target receptors are VEGFR-1 and VEGFR-2), ZD6474 (target receptors are VEGFR-1, VEGFR-2 and VEGFR-3), PTK-787/ZK-222584 (target receptors are VEGFR-1 and VEGFR-2), CEP-7055 (target receptors are VEGFR-1, VEGFR-2 and VEGFR-3), CP-547 (target receptors are VEGFR-1 and VEGFR-2), CP-632 (target receptors are VEGFR-1 and VEGFR-2), GW786024 (target receptors are VEGFR-1, VEGFR-2 and VEGFR-3), AMG706 (target receptors are VEGFR-1, VEGFR-2 and VEGFR-3), Imatinib mesylate (tradename Glivec®/Gleevec®, target receptors are bcr-abl and c-KIT), BMS-214662 (target enzyme is Ras farnesyl transferase), CCI-779 (target enzyme is mTOR), RAD0001 (tradename everolismus®, target enzyme is mTOR), CI-1040 (target enzyme is MEK), SU6668 (target receptors are VEGFR-2, PDGFR-B and FGFR-1), AZD6126, CP547632 (target receptors are VEGFRs), CP868596 GW786034 (target receptors are PDGFRs), ABT-869 (target receptors are VEGFRs and PDGFRs), AEE788 (target receptors are VEGFRs and PDGFRs), AZD0530 (target enzymes are src and abl), and CEP7055.

In yet another preferred embodiment the treatment comprises the administration of chemotherapeutics.

Said chemotherapeutics may be selected from the group consisting of Cyclophosphamid (Endoxan®, Cyclostin®). Adriamycin (Doxorubicin) (Adriblastin®), BCNU (Carmustin) (Carmubris®), Busulfan (Myleran®), Bleomycin (Bleomycin®), Carboplatin (Carboplat®), Chlorambucil (Leukeran®), Cis-Platin (Cisplatin®), Platinex (Platiblastin®), Dacarbazin (DTIC®; Detimedac®), Docetaxel (Taxotere®), Epirubicin (Farmorubicin®), Etoposid (Vepesid®), 5-Fluorouracil (Fluroblastin®, Fluorouracil®), Gemcitabin (Gemzar®), Ifosfamid (Holoxan®), Interferon alpha (Roferon®), Irinotecan (CPT 11, Campto®), Melphalan (Alkeran®), Methotrexat (Methotrexat®, Farmitrexat®), Mitomycin C (Mitomycin®), Mitoxantron (Novantron®), Oxaliplatin (Eloxatine®), Paclitaxel (Taxol®), Prednimustin (Sterecyt®), Procarbazin (Natulan®), Ralitrexed (Tomudex®), Trofosfamid (Ixoten®), Vinblastin (Velbe®), Vincristin (Vincristin®), Vindesin (Eldisine®), Vinorelbin (Navelbine®).

Furthermore, a kit useful for carrying out one of the said methods, comprising at least
a) a primer pair and/or a probe each having a sequence sufficiently complementary to a gene encoding for SPON-1 and/or SPON-2; and/or
b) an antibody directed against SPON-1 and/or SPON-2 is provided.

Furthermore, use of
a) an antibody directed against a ligand from the VEGF family,
b) an antisense nucleic acid or a ribozyme inhibiting the expression of a gene encoding for a ligand from the VEGF family, or
c) an inactive version of a ligand from the VEGF family
as an antagonist for the preparation of a pharmaceutical composition for the treatment of said cancer patients, preferably colorectal cancer patients, identified by a method according to the present invention is provided.

Furthermore, use of
a) an antibody directed against a ligand from the ErbB family,
b) an antisense nucleic acid or a ribozyme inhibiting the expression of a gene encoding for a ligand from the ErbB family, or
c) an inactive version of a ligand from the ErbB family
as an antagonist for the preparation of a pharmaceutical composition for the treatment of said cancer patients, preferably colorectal cancer patients, identified by a method according to the present invention is provided.

In yet another embodiment of the invention a method for correlating the clinical outcome of a patient suffering from or at risk of developing cancer, preferably colorectal cancer, with the presence or non-presence of a defect in expression of at least one gene selected from the group consisting of SPON-1 and/or SPON-2 is provided, said method comprising the steps of:

a) obtaining a (fixed) biological sample from said patient;
b) determining the expression level of at least one of the said marker genes in said patient according to any of the above methods; and
c) correlating the pattern of expression level(s) determined in (b) with said patient's data, said data being selected from the group consisting of etiopathology data, clinical symptoms, anamnesis data and/or data concerning the therapeutic regimen.

The said method is particularly beneficial for epidemiological studies. These studies profit from the fact that large tissue databases exist comprising paraffin and/or formalin fixed tissue samples together with an extensive documentation of the patient's history, including etiopathology data, clinical symptoms, anamnesis data and/or data concerning the therapeutic regimen.

The said methods allow for large scale studies which comprise the correlation of the clinical outcome of a patient suffering from or at risk of developing cancer, preferably colorectal cancer, with the presence or non-presence of a defect in expression of at least one of the marker genes according to the present invention. In order to successfully adopt this approach, the above introduced method for mRNA purification comprising silica coated magnetic beads and chaotropic salts is quite helpful.

Furthermore, a nucleic acid primer pair and/or a nucleic acid probe having a sequence sufficiently complementary to a gene encoding for SPON-1 and/or SPON-2 is provided.

Primer and probe sequences of interest are listed in Table 1.

Moreover, an antibody directed against SPON-1 and/or SPON-2 is provided.

BRIEF DESCRIPTION OF THE EXAMPLES AND DRAWINGS

Additional details, features, characteristics and advantages of the object of the invention are disclosed in the sub-claims, and the following description of the respective figures and examples, which, in an exemplary fashion, show preferred embodiments of the present invention. However, these drawings should by no means be understood as to limit the scope of the invention.

Figures

FIG. 1 demonstrates via Box and Whiskers-Plot the Affymetrix expression analysis of SPON-1 and SPON-2 mRNA from primary tumors of stage IV colorectal cancer patients who received palliative chemotherapy.

Figure 2:
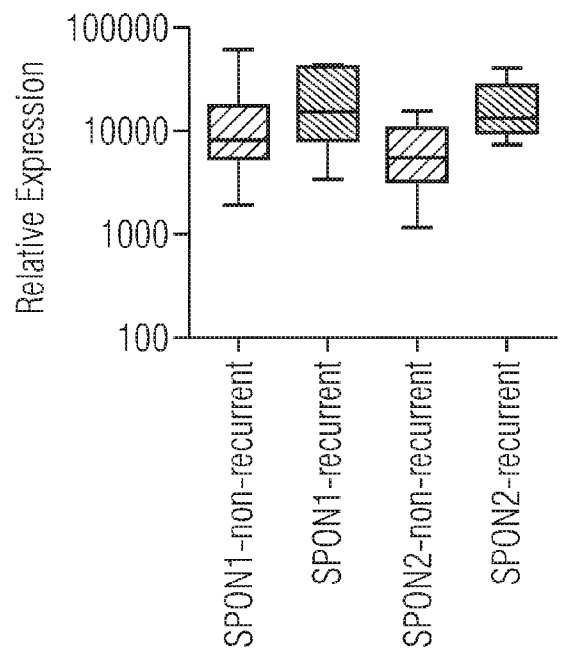

FIG. 2 demonstrates via Box and Whiskers-Plot the Affymetrix expression analysis of SPON-1 and SPON-2 mRNA from primary tumors of stage III colorectal cancer patients who received adjuvant chemotherapy.

Figure 3:
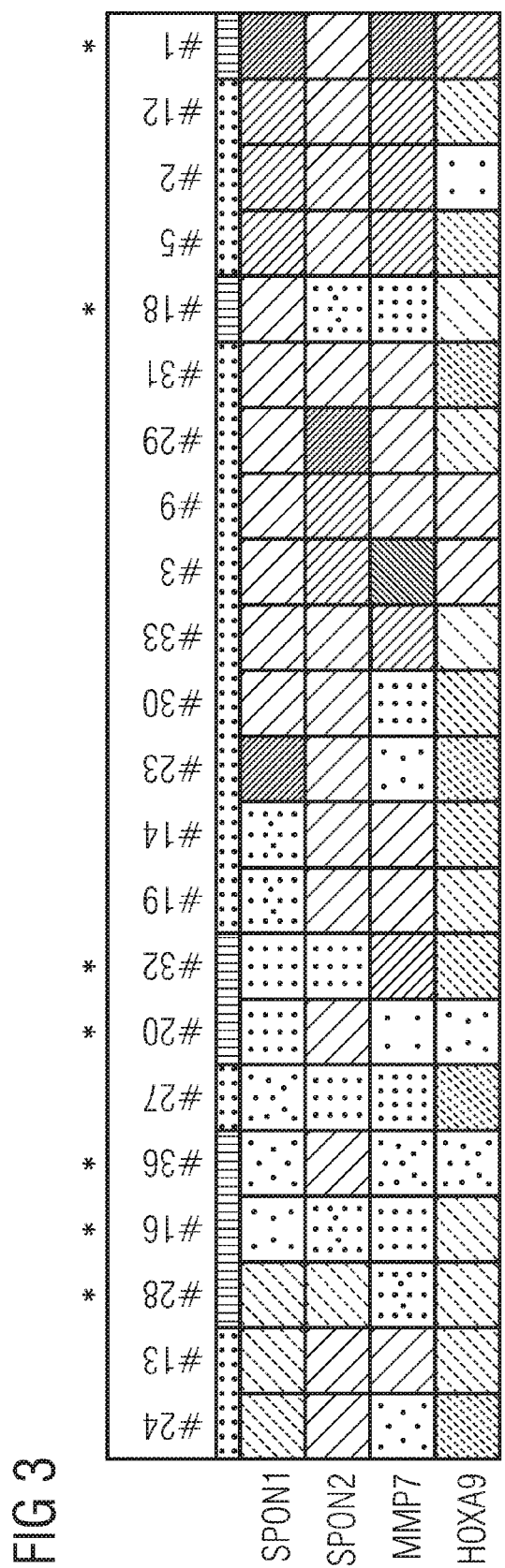

FIG. 3 demonstrates microarray analysis of SPON-1, SPON-2, MMP7 (matrix metalloproteinase 7) and HOXA9 (homebox A9) gene expression in stage III colorectal cancer patients. The patients' data are ordered by the decreasing expression of SPON-1 from left to right.

Figure 4:
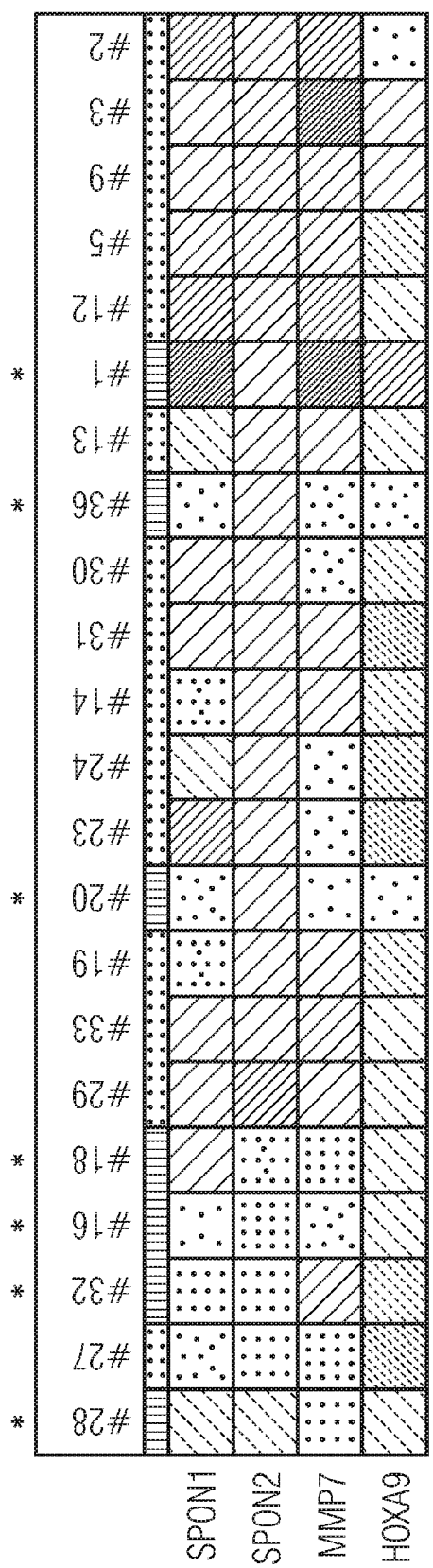

FIG. 4 demonstrates microarray analysis of SPON-1, SPON-2, MMP7 and HOXA9 gene expression in stage III colorectal cancer patients. The patients' data are ordered by the decreasing expression of SPON-2 from left to right.

EXAMPLE

Patients and Tumor Characteristics

The study was approved by the ethics committee of the University of Erlangen-Nuremberg. Written consent was obtained from eligible patients, and the research was conducted in accordance with the principles of the Declaration of Helsinki.

In the first study cohort biopsy samples from the primary tumor and one or more synchronous liver metastases were collected intraoperatively from N=25 patients with UICC stage IV colorectal carcinoma at the time of resection of the primary tumor. Additionally, 10 of those additional patients contributed fresh biopsies from the primary colorectal cancer liver metastases. Fresh frozen Material from the primary tumors was not available from N=16 patients, so they were excluded from the comparative analyses between primary and metastatic tumor. Locations of the primary tumors were as follows: rectum (8 patients), sigmoid colon (5 patients), ascending and transverse colon (3 patients), descending colon/cecum (3 patients). Rectal cancer was defined in both study cohorts according to the definition of the international documentation system (IDS) as elaborated in the Working Party Report to the World Congresses of Gastroenterology.

Chemotherapy

Patients received in outpatient care either 500 mg/m$^2$ FA together with 2,600 mg/m$^2$ 5-FU i.v. administered as a 24-h infusion once weekly (according to the "Arbeitsgemeinschaft Internistische Onkologie" (AIO) regimen) applied via a miniature pump system or the above mentioned 5-FU/FA regimen together with biweekly application of 85 mg/m$^2$ Oxaliplatin i.v. One cycle comprised six weekly infusions followed by two weeks of rest.

For non-metastatic patients it has been routinely examined whether they have developed recurrences.

In the case of therapy control and good tolerability chemotherapy was applied for metastatic patients until progress or the time of secondary metastatic resection. After every cycle, a follow-up examination comprising a blood count, serum test for carcinoembryonic antigen (CEA) and cancer antigen (CA) 19-9, an abdominal CT scan and a chest X-ray were performed. Response to chemotherapy was evaluated in all cases after each cycle of chemotherapy in accordance with WHO criteria. Response to chemotherapy was evaluated in all patients by CT scans. Partial remission (PR) was defined as a maximum of reduction in the size of a reference metastasis of at least 50% during chemotherapy with complete remission (CR) showing no metastatic material found anymore. Stable disease (SD) was defined as a maximum reduction in size of less than 50% to an increase in size of less than 25% with a progressive disease (PD) showing an increase of at least 25% in size.

Sample Preparation

Intraoperatively obtained biopsies from colorectal primary tumors and liver metastases were shock-frozen with liquid nitrogen immediately (within one minute after removal) and then stored at −80° C. The frozen tissues were cut into 8 □m sections using a cryostat and then stained with hematoxylin and eosin for histological examination. Laser capture microdissection (LCM) was performed immediately after staining and dehydration. Tumor areas of interest were selected with the help of an experienced pathologist (A.D.) and excised using a 0.6 mm laser beam (32 mW, 30 Hz, 0.8 sec pulse). Each sample yielded approximately 10.000 cells. Captured cells were dissolved in RLT buffer (RNeasy Mini Kit, Qiagen, Hilden, Germany) and RNA was extracted as described below. Tumor material from two colon primary tumors and one liver metastasis were differentially microdissected into stromal cells and tumor cells.

RNA Extraction

Total RNA was isolated with the use of commercial kits (RNeasy-Mini Kit; Qiagen, Hilden, Germany) according to the manufacturer's instructions. As part of this procedure, DNAse digestion (Qiagen, Hilden, Germany) was included before elution from the columns. The quantity and quality of the purified total RNA was measured with the use of the RNA Nano 6000 Assay Chip (Bioanalyzer 2100; Agilent Technologies, Palo Alto, Calif.).

RNA Amplification

Each biopsy yielded up to 800 ng of total RNA. After several rounds of T7 promotor-based RNA amplification, each sample typically provided a final yield of 50-100 □g of amplified RNA (aRNA). We performed reverse transcription with the MessageAmp aRNA Kit (Ambion, Huntingdon, United Kingdom) followed by in vitro transcription according to the "Eberwine-method (van Geldern R N et al., 1990)[7]. During this later step a biotin label was added. The overall quality of the aRNA was assessed using the RNA Nano 6000 Assay Chip.

GeneChip Hybridisation

Samples were hybridised to Affymetrix HG U133-A high-density oligonucleotide-based arrays (Affymetrix, Santa Clara/Calif., USA) targeting 22,230 human genes and expressed sequence tags (EST). From each biopsy, 15 □g of either cRNA or aRNA was loaded onto an array following the recommended procedures for prehybridization, hybridization, washing and staining with streptavidin-phycoerythrin. The arrays were scanned on an Affymetrix GeneChip Scanner (Agilent, Palo Alto, Calif.). The fluorescence intensity was measured for each microarray and normalised to the average fluorescence intensity of the entire microarray.

Statistical Analysis

The raw, unnormalized data-sets were analyzed by MicroArray Suite (Affymetrix) for normalization and estimation of expression values. Signal intensities and detection calls for statistical analysis and hierarchical clustering were determined using the GeneChip 5.0 software (Affymetrix) and Expressionist™ software (Genedata). Unsupervised two-dimensional hierarchical cluster analysis of the candidate gene data were done using the between-groups linkage method with the □$^2$ measure for ordinal data to identify individual groups of tumours with specific SPON-1 and/or SPON-2 profiles. Significance levels of microarray results for responding vs. non-responding Stage IV colorectal cancer or recurrent vs. non-recurrent Stage III colorectal cancer were calculated using the Mann-Whitney U-test. A p value of <0.05 was regarded as significant.

For box plots, the median expression values as well as the first and third quartiles were calculated. Variances between box blots were calculated using the F-test. A p value of <0.05 was regarded as significant.

RNA from FFPE Probes

Two 10 µm thick sections were cut from each paraffin block for molecular analysis of gene expression. For all tumor samples included in the analysis the number of malignant cells represented at least 50% of all nucleated cells as judged by hematoxylin-eosin staining. The mRNA was extracted by means of an experimental method based on proprietary magnetic beads from Siemens Medical Solutions. The FFPE slide is deparraffinized in xylol and ethanol, the pellet is washed with ethanol and dried at 55° C. for 10 minutes. The pellet is then lysed and proteinized overnight at 55° C. with shaking. After adding a binding buffer and the magnetic particles (Siemens Medical Solutions Diagnostic GmbH, Leverkusen, Germany) nucleic acids are bound to the particles within 15 minutes at room temperature. On a magnetic stand the supernatant is taken away and beads can be washed several times with washing buffer. After adding elution buffer and incubating for 10 min at 70° C. the supernatant is taken away on a magnetic stand without touching the beads. After normal DNAse I treatment for 30 min at 37° C. and inactivation of DNAse I the solution is used for reverse transcription-polymerase chain reaction (RT-PCR).

The quality and quantity of RNA was checked by measuring absorbance at 260 nm and 280 nm. Pure RNA has an A260/A280 ratio of 1.9-2.0. Transcriptional activity of the genes was assessed with quantitative Reverse Transcriptase TaqMan™ polymerase chain reaction (RT-PCR) analysis. The inventors applied 40 cycles of nucleic acid amplification and adjusted RNA amounts used for each reaction according to a calculated RPL37A housekeeping gene expression level at a cycle threshold (CT) old (CT) of 28. A normalized $2^{(40-\Delta CT)}$ copy number value was calculated that correlates proportionally to RNA transcription levels. Alternatively ACT could be calculated as 40–(CT target gene–CT housekeeping gene). For each of the genes RNA-specific Primer/Probe were designed to detect all isoforms simultaneously. Expression of each gene was defined as high and low according to values above and up to the median, respectively.

Results

By correlation analysis, the inventors of the present invention have found that overexpression of SPON-1 and/or SPON-2 as assessed by Affymetrix and PCR analysis indicates poor response to chemotherapy and worse overall survival in stage IV colorectal cancer. The Box and Whiskers analysis (FIG. 1, PR=partial remission; SD=stable disease; PD=progressive disease) demonstrates for stage IV colorectal cancer patients who received palliative chemotherapy a positive correlation of an upregulated SPON-1 and/or SPON-2 mRNA expression and a stable disease and progressive disease, respectively. In contrast, it could be demonstrated as well a correlation of a downregulated SPON-1 and/or SPON-2 mRNA expression and a partial remission of primary tumors.

Via Box and Whiskers analysis it could be demonstrated for SPON-1 a trend regarding stage III colorectal cancer to predict early recurrence despite adjuvant chemotherapy treatment (FIG. 2). However, for SPON-2 it could be demonstrated a significant correlation of an upregulated mRNA expression and recurrence, respectively, and a significant correlation of a downregulated mRNA expression and non-recurrence (Mann-Whitney test, p=0.03; n=16) (FIG. 2). Therefore, SPON-2 is a more appropriate marker to discriminate recurrent versus non-recurrent stage III colorectal tumors.

Said statement can be further strengthened by comparison of the expression data of SPON-1 and SPON-2 in stage III colorectal cancer patients (FIGS. 3 and 4, patients with a recurrent disease are marked with an asterisk*, and patients with a non-recurrent disease are not marked with an asterisk*). By use of SPON-2 as gene marker patients with a recurrent diesease could be identified improved compared to SPON-1.

The inventors have found by using Spearman Rho correlation that there is a strong correlation between SPON-1 and SPON-2, and that there is a positive relationship between these two variables (Table 2).

Discussion

By expression analysis of SPON-2, optionally combined with SPON-1, an improved molecular test to select a more appropriate therapy can be provided.

To validate the molecular signature of metastases as far as drug sensitivity or resistance is concerned, the results should be verified in a study with a large independent cohort of patients.

Interestingly, SPON-1 has been identified to be upregulated in ovarian cancer (Pyle-Chenault et al., 2005)[8]. In normal ovary, VEGF appears to play a major role in the formation of new vessels by stimulating endothelial cell proliferation and migration (Hazzard and Stouffer, 2000)[9]. The identification of SPON-1 in normal bovine ovarian follicular fluid (Miyamoto et al., 2001)[10] indicates that SPON-1 may complement VEGF activity during angiogenesis. Pyle-Chenault et al. concluded that endothelial cell and smooth muscle cell growth factors would be highly expressed in areas undergoing significant angiogenesis. Since angiogenesis is also required to support tumor growth, it is not surprising that both VEGF (Wang et al., 2002; Yamamoto et al., 1997; Fujimoto et al., 1998)[11,12,13] and SPON-1 are overexpressed in ovarian cancers. These conclusions may be transferred from ovarian cancer to colorectal cancer.

Since it is very difficult to determine those tumor types which are promoted by EGFR overexpression, the inventors of the present invention have for the first time suggested not to use the targets themselves as marker genes, but SPON-2, optionally combined with SPON-1, as marker genes to predict the clinical response of a patient suffering from or at risk of developing colorectal cancer towards a medicament related to the signalling pathway of receptors from the ErbB receptor family.

Disclaimer

To provide a comprehensive disclosure without unduly lengthening the specification, the applicant hereby incorporates by reference each of the patents and patent applications referenced above.

The particular combinations of elements and features in the above detailed embodiments are exemplary only; the interchanging and substitution of these teachings with other teachings in this and the patents/applications incorporated by reference are also expressly contemplated. As those skilled in the art will recognize, variations, modifications, and other implementations of what is described herein can occur to those of ordinary skill in the art without departing from the spirit and the scope of the invention as claimed. Accordingly, the foregoing description is by way of example only and is not intended as limiting. The invention's scope is defined in the following claims and the equivalents thereto. Furthermore, reference signs used in the description and claims do not limit the scope of the invention as claimed.

TABLE 1

Primer and Probe Sequences of Interest

| Internal number | Gene | NM_number | Probe | Forward primer | Reverse primer |
|---|---|---|---|---|---|
| SC045 (SEQ ID NOs: 1-3) | SPON-1 | NM_006108 | CGGGAACCAGCTACCGCGTAACAC | GCGACCCCGACTTCTACAAG | GGAGGGAGGAGCAGCTGAA |
| SC297 (SEQ ID NOs: 4-6) | SPON-1 | NM_006108 | CCTACCTGCCGCACCCTGGGACT | ACCATGTCTGGAAGTGACTATGCC | AATCTGCTGTCTTCATCTGTGAATGT |
| SC298 (SEQ ID NOs: 7-9) | SPON-1 | NM_006109 | AGAGTCATGTTACCCATTCTTAGCCATTAACCTGG | CATTTTAAAATCCTGATTTTGGAGACTTA | GCTTCTTATAAATTCCCCATTGCA |
| SC299 (SEQ ID NOs: 10-12) | SPON-2 | NM_012445 | TGTAGACAGCGCCTCAGTTCCAGAAACG | CCCAGCAGGGACAATGAGA | AGACCTCGCAGTCCAGCG |
| SC300 (SEQ ID NOs: 13-15) | SPON-2 | NM_012446 | CCCTCTGGTGGCCGGCACG | CCGACCATCTCTGCACTGAA | AGAAGCAAGGTTGGGAAAGGA |

TABLE 2

Spearman Rho correlation between SPON-1 and SPON-2

| Variable 1 | Variable 2 | Spearman Rho |
|---|---|---|
| SPON-1 SC_297_manual | SPON-1 SC_45_manual | 0.7335 |
| SPON-2 SC_299_manual | SPON-1 SC_45_manual | 0.5447 |
| SPON-2 SC_299_manual | SPON-1 SC_297_manual | 0.1677 |
| SPON-2 SC_300_manual | SPON-1 SC_45_manual | 0.5940 |
| SPON-2 SC_300_manual | SPON-1 SC_297_manual | 0.2885 |
| SPON-2 SC_300_manual | SPON-2 SC_299_manual | 0.8132 |

REFERENCES

1. Wein A et al., Ann Oncol 2001; 12: 1721-7.
2. Goldberg R M et al, J Clin Oncol 2006; 24:3347-53.
3. Hurwirz H., Clin Colorectal Cancer 2004; 4 Suppl.: 562-8.
4. Schrag D, N Engl J Med 2004; 351: 317-9.
5. Shepherd F A, N Engl J Med 2005; 353(2):123-32.
6. Brueckl W M et al., JCO 2007; 25(18S): 4112.
7. van Geldern R N et al., PNAS USA 1990; 87: 1663-7.
8. Pyle-Chenault R A et al., Tumor Biol 2005; 26: 245-257.
9. Hazzard T M and Stouffer R L, Baillieres Best Pract Res Clin Obstet Gynaecol 2000; 14: 883-900.
10. Miyamoto K et al., Arch Biochem Biophys 2001; 390: 93-100.
11. Wang J et al., Int J Cancer 2002; 97: 163-167.
12. Yamamoto S et al., Br J Cancer 1997; 76: 1221-1227.
13. Fujimoto J et al., Cancer 1998; 83: 2528-2533.

What is claimed is:

1. A collection of nucleic acid reagents comprising at least one primer pair/probe set selected from the group consisting of:
   (a) a primer consisting of SEQ ID NO: 2, a primer consisting of SEQ ID NO: 3, and a probe consisting of SEQ ID NO: 1;
   (b) a primer consisting of SEQ ID NO: 5, a primer consisting of SEQ ID NO: 6, and a probe consisting of SEQ ID NO: 4;
   (c) a primer consisting of SEQ ID NO: 8, a primer consisting of SEQ ID NO: 9, and a probe consisting of SEQ ID NO: 7;
   (d) a primer consisting of SEQ ID NO: 11, a primer consisting of SEQ ID NO: 12, and a probe consisting of SEQ ID NO: 10; and
   (e) a primer consisting of SEQ ID NO: 14, a primer consisting of SEQ ID NO: 15, and a probe consisting of SEQ ID NO: 13.

* * * * *

SEQUENCE LISTING

<160> NUMBER OF SEQ ID NOS: 15

<210> SEQ ID NO 1
<211> LENGTH: 24
<212> TYPE: DNA
<213> ORGANISM: Artificial
<220> FEATURE:
<223> OTHER INFORMATION: SPON-1

<400> SEQUENCE: 1
cgggaaccag ctaccgcgta acac                                            24

<210> SEQ ID NO 2
<211> LENGTH: 20
<212> TYPE: DNA
<213> ORGANISM: Artificial
<220> FEATURE:
<223> OTHER INFORMATION: SPON-1

<400> SEQUENCE: 2
gcgaccccga cttctacaag                                                 20

<210> SEQ ID NO 3
<211> LENGTH: 19
<212> TYPE: DNA
<213> ORGANISM: Artificial
<220> FEATURE:
<223> OTHER INFORMATION: SPON-1

<400> SEQUENCE: 3
ggagggagga gcagctgaa                                                  19

<210> SEQ ID NO 4
<211> LENGTH: 23
<212> TYPE: DNA
<213> ORGANISM: Artificial
<220> FEATURE:
<223> OTHER INFORMATION: SPON-1

<400> SEQUENCE: 4
cctacctgcc gcaccctggg act                                             23

<210> SEQ ID NO 5
<211> LENGTH: 24
<212> TYPE: DNA
<213> ORGANISM: Artificial
<220> FEATURE:
<223> OTHER INFORMATION: SPON-1

<400> SEQUENCE: 5
accatgtctg gaagtgacta tgcc                                            24

<210> SEQ ID NO 6
<211> LENGTH: 26
<212> TYPE: DNA
<213> ORGANISM: Artificial
<220> FEATURE:
<223> OTHER INFORMATION: SPON-1

<400> SEQUENCE: 6
aatctgctgt cttcatctgt gaatgt                                          26

<210> SEQ ID NO 7
<211> LENGTH: 35
<212> TYPE: DNA

```
<213> ORGANISM: Artificial
<220> FEATURE:
<223> OTHER INFORMATION: SPON-1

<400> SEQUENCE: 7
agagtcatgt tacccattct tagccattaa cctgg                              35

<210> SEQ ID NO 8
<211> LENGTH: 29
<212> TYPE: DNA
<213> ORGANISM: Artificial
<220> FEATURE:
<223> OTHER INFORMATION: SPON-1

<400> SEQUENCE: 8
cattttaaaa tcctgatttt ggagactta                                     29

<210> SEQ ID NO 9
<211> LENGTH: 24
<212> TYPE: DNA
<213> ORGANISM: Artificial
<220> FEATURE:
<223> OTHER INFORMATION: SPON-1

<400> SEQUENCE: 9
gcttcttata aattccccat tgca                                          24

<210> SEQ ID NO 10
<211> LENGTH: 28
<212> TYPE: DNA
<213> ORGANISM: Artificial
<220> FEATURE:
<223> OTHER INFORMATION: SPON-2

<400> SEQUENCE: 10
tgtagacagc gcctcagttc cagaaacg                                      28

<210> SEQ ID NO 11
<211> LENGTH: 19
<212> TYPE: DNA
<213> ORGANISM: Artificial
<220> FEATURE:
<223> OTHER INFORMATION: SPON-2

<400> SEQUENCE: 11
cccagcaggg acaatgaga                                                19

<210> SEQ ID NO 12
<211> LENGTH: 18
<212> TYPE: DNA
<213> ORGANISM: Artificial
<220> FEATURE:
<223> OTHER INFORMATION: SPON-2

<400> SEQUENCE: 12
agacctcgca gtccagcg                                                 18

<210> SEQ ID NO 13
<211> LENGTH: 19
<212> TYPE: DNA
<213> ORGANISM: Artificial
<220> FEATURE:
<223> OTHER INFORMATION: SPON-2

<400> SEQUENCE: 13
ccctctggtg gccggcacg                                                19
```

```
<210> SEQ ID NO 14
<211> LENGTH: 20
<212> TYPE: DNA
<213> ORGANISM: Artificial
<220> FEATURE:
<223> OTHER INFORMATION: SPON-2

<400> SEQUENCE: 14
ccgaccatct ctgcactgaa                                              20

<210> SEQ ID NO 15
<211> LENGTH: 21
<212> TYPE: DNA
<213> ORGANISM: Artificial
<220> FEATURE:
<223> OTHER INFORMATION: SPON-2

<400> SEQUENCE: 15
agaagcaagg ttgggaaagg a                                            21
```